US006921390B2

(12) United States Patent
Bucay-Couto et al.

(10) Patent No.: US 6,921,390 B2
(45) Date of Patent: Jul. 26, 2005

(54) LONG-TERM INDWELLING MEDICAL DEVICES CONTAINING SLOW-RELEASING ANTIMICROBIAL AGENTS AND HAVING A SURFACTANT SURFACE

(75) Inventors: Weenna Bucay-Couto, Bedford, MA (US); Jamie (Jianmin) Li, Lexington, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 300 days.

(21) Appl. No.: 09/911,051

(22) Filed: Jul. 23, 2001

(65) Prior Publication Data

US 2003/0018306 A1 Jan. 23, 2003

(51) Int. Cl.$^7$ ............................ A61M 5/32; A61M 25/00
(52) U.S. Cl. ........................................ 604/265; 604/544
(58) Field of Search ................... 604/265–266, 604/891.1, 502, 523–527, 288.01–288.04, 544, 82, 6.16, 85; 623/1.42–1.48, 23.64, 23.66, 23.7; 424/422, 423, 450–452, 489–490

(56) References Cited

U.S. PATENT DOCUMENTS

| | | | |
|---|---|---|---|
| 4,917,686 A | | 4/1990 | Bayston et al. ............. 604/265 |
| 5,156,164 A | * | 10/1992 | LeVeen et al. ............. 128/832 |
| 5,344,411 A | * | 9/1994 | Domb et al. ............ 128/207.14 |
| 5,466,675 A | | 11/1995 | Piljac et al. .................. 514/25 |
| 5,626,862 A | * | 5/1997 | Brem et al. ................. 424/1.11 |
| 5,824,359 A | | 10/1998 | Khan et al. ................. 427/2.3 |
| 5,855,913 A | * | 1/1999 | Hanes et al. ................. 424/43 |
| 5,874,064 A | * | 2/1999 | Edwards et al. ............. 424/45 |
| 5,965,524 A | | 10/1999 | Burke, Jr. et al. ............. 514/9 |
| 5,985,309 A | * | 11/1999 | Edwards et al. ............ 424/426 |
| 6,051,552 A | | 4/2000 | Reid et al. .................... 514/8 |
| RE37,053 E | * | 2/2001 | Hanes et al. ................. 424/43 |
| 6,316,018 B1 | * | 11/2001 | Ding et al. ................. 424/423 |
| 2003/0036761 A1 | * | 2/2003 | Smothers et al. ............ 606/72 |

FOREIGN PATENT DOCUMENTS

| | | | | |
|---|---|---|---|---|
| EP | 0879595 A2 | * | 11/1998 | |
| EP | 0879 595 A2 | | 11/1998 | ............. A61K/9/00 |
| WO | WO 99/25190 | | 5/1999 | ........... A01N/33/12 |
| WO | WO 99/32168 | * | 7/1999 | |
| WO | WO 99/47187 | | 9/1999 | ............ A61L/29/00 |
| WO | WO 00/71139 A2 | | 11/2000 | ........... A61K/35/00 |
| WO | WO 02/12271 A2 | | 2/2002 | ............. C07K/7/00 |

OTHER PUBLICATIONS

Millsap, et al. "Adhesion of Lactobacillus species in urine and phosphate buffer to silicone rubber and glass under flow".*

Velraeds, et al. "Inhibition of initial adhesion of uropathogenic enterococcus faecalis to solid substrata by an adsorbed biosurfactant layer from lactobacillus acidophilus."*

Vacheethasanee. "Student Research Award in the Ph.D. Degree Candidate Category, World Biomaterials Congress 2000 ".*

Vacheethasanee et al, Surfactant Polymers Designed to Suppress Bacterial Adhesion on Biomaterials.*

(Continued)

*Primary Examiner*—Nicholas D. Lucchesi
*Assistant Examiner*—Catherine S. Williams
(74) *Attorney, Agent, or Firm*—Mayer Fortkort & Williams PC; David B. Bonham, Esq.

(57) ABSTRACT

A medical device for long-term implantation is provided, as well as a method of making the same and a method of treatment using the same. The medical device comprises (1) a reservoir including (a) a polymer matrix and (b) an antimicrobial agent disposed within the polymer matrix, wherein the reservoir is adapted for long-term release of the antimicrobial agent from the polymer matrix; and (2) a surfactant region disposed over the reservoir at an outer surface of the device.

28 Claims, 2 Drawing Sheets

OTHER PUBLICATIONS

Hashimoto, H., et al., "Basic Study on anti–bacterial urethral catheter. I. Development of a new anti–bacterial coating material for silicon catheters",Abstract, Department of Urology, Okayama University School of Medicine, Kansenshogaku Zasshi, May 2000; 74(5): 431–40.

Velraeds, Martine M.C. et al., "Inhibition of Initial Adhesion of Uropathogenic Enterococcus Faecalis to Solid Substrata By An Adsorbed Biosurfactant Layer From Lactobacillus Acidophilus",Urology 49 (5), 1997, pp. 790–794.

Vacheethasanee, Katanchalee et al., "Surfactant Polymers designed to suppress bacterial (*Staphylococcus epidermidis*) adhesion on biomaterials", J Biomed Mater Res, 50, 302–312, 2000.

Velraeds,, Martine M. C. et al., "Inhibition of initial adhesion of uropathogenic *Enterococcus faecalis* by biosurfactants from *Lactobacillus isolates*," Appl Environ Microbiol, Jun. 1996; 1958–63.

Millsap, K.W., et al. "Adhesion of Lactobacillus species in urine and phosphate buffer to silicone rubber and glass under flow," Biomaterials 18(1996), pp. 87–91.

Velraeds, Martine M.C., et al., "Interference in initial adhesion of uropathogenic bacteria and yeasts to silicone rubber by a *Lactobacillus acidophilus* biosurfactant", J Med Microbiol, vol. 47, 1998, pp. 1081–1085.

Howard Jeffrey C., et al., "Identification of Collagen–Binding Proteins in Lactobacillus spp. with Surface–Enhanced Laser Desorption/Ionization–Time of Flight ProteinChip Technology",Appl Environmental Microbiology, Oct. 2000, pp. 4396–4400.

Heinemann, Christine et al., "Purification and characterization of a surface–binding protein from *Lactobacillus fermentum* RC–14 that inhibits adhesion of *Enterococcus Faecalis* 1131", FEMS Microbiology Letters 190 (2000), pp. 177–180.

* cited by examiner

LONG-TERM INDWELLING MEDICAL DEVICES CONTAINING SLOW-RELEASING ANTIMICROBIAL AGENTS AND HAVING A SURFACTANT SURFACE

FIELD OF THE INVENTION

The present application relates to long-term, indwelling medical devices.

BACKGROUND OF THE INVENTION

Polymeric materials for indwelling devices that can resist biofilm formation and encrustation over long time periods are presently in high demand.

One region of the body that is of particular interest is the urinary system. In theory, the colonization of an indwelling-device surface with urease-producing bacteria will lead to the hydrolysis of urea into ammonium and carbonate, causing alkalinization of urine in the vicinity of the device. The higher pH environment in turn lowers the solubility of struvite and hydroxyapatite found within the urine, leading to the formation of deposits on the device surface. Clinical and experimental studies have focused on several treatments to avoid the formation of such deposits, including the following: (a) acidification of urine, (b) modification of the device surface to provide a smoother and more hydrophilic surface (using, for example, lubricious hydrophilic coatings, phospholipid coatings or surfactant coatings), and (c) formation of surface coatings with one or more antimicrobials (for example, urinary stents have been immersed in antibiotic or prior to use and have been provided with antimicrobial coatings).

These efforts, however, have been ineffective to significantly prolong the half-life of indwelling stents. In general, the proportion of the stent covered with biofilm increases with time, as does the degree of encrustation. Moreover, studies have shown that adherent bacteria inside the biofilm are resistant to antimicrobial treatments. Typically, the doses required to kill biofilm bacteria (e.g., adherent bacteria protected by a glycocalyx biofilm matrix) is many times the dose required to eradicate planktonic bacteria (i.e., non-adherent bacteria). Such elevated doses are also typically toxic to the patient.

SUMMARY OF THE INVENTION

According to an embodiment of the invention, a medical device for long-term implantation is provided which comprises: (1) a reservoir including (a) a polymer matrix and (b) an antimicrobial agent disposed within the polymer matrix, wherein the reservoir is adapted for long-term release of the antimicrobial agent from the polymer matrix; and (2) a surfactant region disposed over the reservoir at an outer surface of the device.

Preferred surfactants for the practice of the present invention include biosurfactants and surfactant polymers. Preferred biosufactants include glycolipids, lipopeptides, depsipeptides, phospholipids, substituted fatty acids, and lipopolysaccharides. Further preferred biosurfactant include surlactin, surfactin, visconsin and rhamnolipids. Preferred surfactant polymers include surfactant polymers having a poly(vinyl amine) backbone and having hydrophilic poly(ethylene oxide) sides chains and hydrophobic hexanal side chains.

Preferred antimicrobial agents include for the practice of the present invention triclosan, chlorhexidine, silver sulfadiazine, silver ions, benzalkonium chloride and zinc pyrithione. Further preferred antimicrobial agents include broad-spectrum antibiotics and antiseptic agents.

Preferred polymer matrices for the practice of the present invention are those that comprise an ethylene-vinyl acetate copolymer and those that comprise polyurethane.

Preferred devices include ureteral stents and urethral catheters.

In some cases, a barrier layer is provided between the polymer matrix and the surfactant region.

According to another embodiment of the invention a method of treatment is provided that comprises: (1) providing a medical device, which further comprises (a) a reservoir, which includes a polymer matrix portion and an antimicrobial agent disposed within the polymer matrix portion; and (b) a surfactant region disposed over the reservoir at an outer surface of the device; and (2) implanting the medical device within the body of a patient for a period of at least three months.

Patients appropriate for the practice of the present invention include animal patients, preferably mammals, and more preferably humans. One preferred location for implantation is in a urine-contacting area.

According to another embodiment of the invention, a method of constructing a medical device is provided. The method comprises: (1) forming a reservoir, which includes (a) a polymer matrix portion and (b) an antimicrobial agent disposed within the polymer matrix portion; and (2) providing a surfactant region over the reservoir at an outer surface of the device.

In some embodiments, the antimicrobial agent is provided within the polymer matrix at the time of formation of the polymer matrix. For instance, the antimicrobial agent may be co-cast with the polymer matrix, or the antimicrobial agent may be co-extruded with the polymer matrix. In other instances, the antimicrobial agent is provided within the polymer matrix by imbibing the antimicrobial agent into the polymer matrix.

The surfactant can be adhered to the outer surface of the device based on hydrophobic interactions, ionic interactions and/or covalent interactions.

One advantage of the present invention is that medical devices can be created, which retard biofilm formation and encrustation over long periods of time.

Another advantage of the present invention is that such medical devices are of relatively simple design and can be produced using relatively simple techniques.

These and other embodiments and advantages of the present invention will become immediately apparent to those of ordinary skill in the art upon review of the Detailed Description and claims to follow.

DETAILED DESCRIPTION OF THE INVENTION

In accordance with an embodiment of the present invention, a dual approach is used to provide an implantable medical device having long-term bacterial clearance. In accordance with one approach, the surface properties of the device are modified through the use of a surfactant. In accordance with the other approach, antimicrobial agents are released from the device in a slow-release fashion upon implantation.

Figure 1:
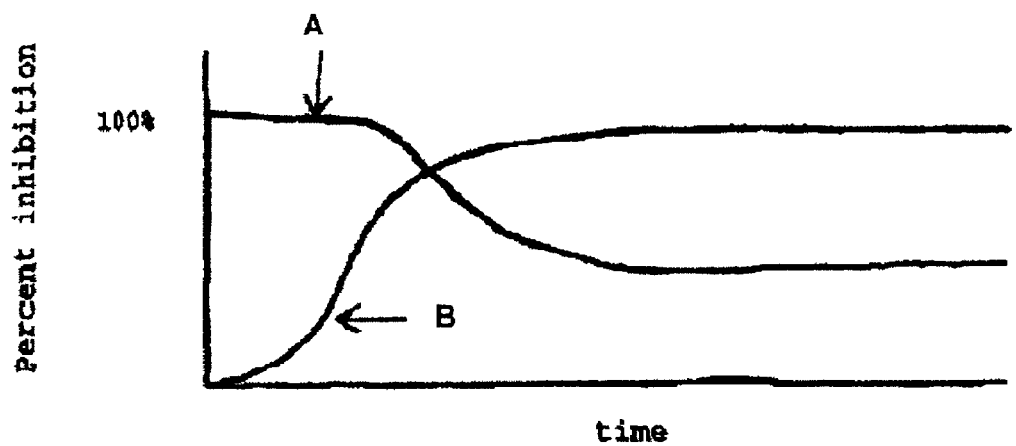
FIG. 1 illustrates the general patterns of inhibition of bacterial adhesion on the surface of a medical device that are due to (a) the modification of the device surface with a surfactant and (b) the long-term release of antimicrobial agent from the device.

FIG. 1 illustrates the general patterns of bacterial adhesion inhibition that is due to each of the above approaches. The pattern of bacterial adhesion inhibition that is due to the modification of the device surface with a surfactant is illustrated in curve "A" of FIG. 1. As can be seen from this curve, at the outset, the surfactant-modified surface resists adherence of living bacteria (as well as dead bacteria and host protein) to a high degree. However, due to degradation of the surfactant, the efficacy associated with the surfactant-modified surface eventually decreases over time. On the other hand, the pattern of bacterial adhesion inhibition that is due to the long-term release of antimicrobial agents is illustrated in FIG. 1 as curve "B". As seen from this curve, the antimicrobial agent release is initially negligible. However, antimicrobial agent eventually blooms to the surface of the medical device, killing bacteria in a sustained manner and thus preventing living bacteria from actively colonizing the medical device. The cumulative effect of these two approaches is a continuous process whereby bacterial adhesion is inhibited over a long period of time.

Figure 2:
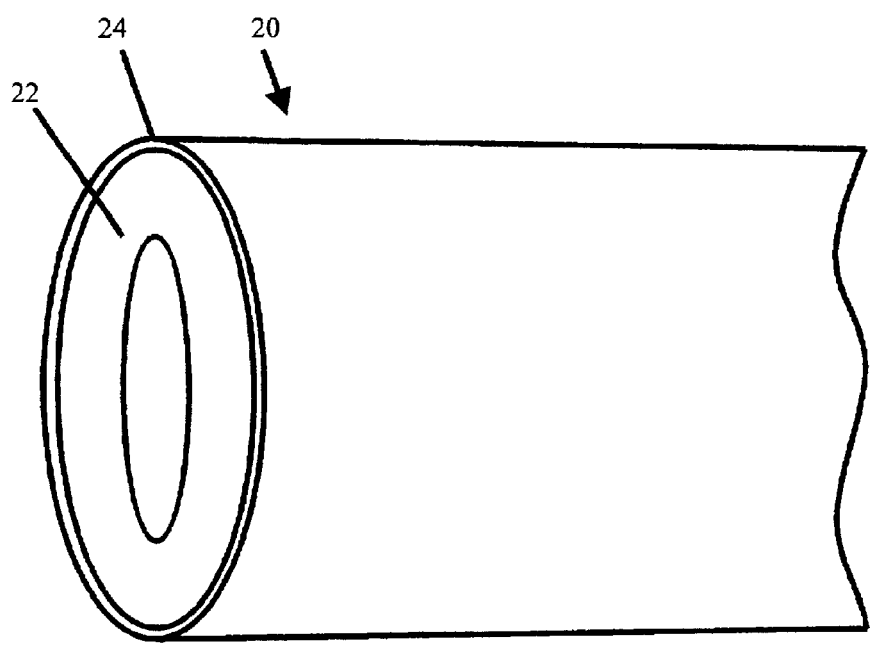
FIG. 2 and FIG. 3 are schematic representations of medical devices in accordance with two embodiments of the invention.

An example of a medical device design that embodies this approach is presented in FIG. 2. Referring now to this figure, the overall medical device (in this case, a tubular portion of a medical device) is generally represented by the numeral 20. The medical device 20 includes a polymer matrix portion 22, within which is disposed one or more broad-spectrum antimicrobial agents. In this way, when loaded with broad-spectrum antimicrobial agents, the polymer matrix portion 22 acts as a slow-release reservoir, or depot, for the antimicrobial agents. A surfactant region 24 is disposed over the polymer matrix portion 22 at the surface of the device 20.

Such a medical device is useful for long-term indwelling applications due to its ability to resist biofilm formation and encrustation. As used herein, "long-term" is greater than 3 months, and preferably greater than 6 months and more preferably greater than 1 year. Subjects for treatment via implantation are preferably mammalian subjects and more preferably human subjects.

Essentially any implantable medical device which experiences biofilm formation and/or encrustation is appropriate for the practice of the present invention, including urine contacting devices (for example, ureteral stents, urinary catheters and drug delivery devices), blood contacting devices (including cardiovascular stents, venous access devices, valves, vascular grafts, hemodialysis and biliary stents), and body tissue and tissue fluid contacting devices (including biosensors, implants and artificial organs).

As used herein, an "antimicrobial agent" is any agent that is harmful to microbes, especially pathogenic bacteria. Preferred broad-spectrum antimicrobial agents for the present invention include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides, and antiseptics such as iodine, methenamine, nitrofurantoin, validixic acid and other acidifying agents, including acids extracted from cranberry juice.

Polymers for use in the polymer matrix portion include essentially any polymer that is compatible with the implantation environment and that allows for the release of the antimicrobial agent. Such polymers may be crosslinked or uncrosslinked, linear or branched, natural or synthetic, thermoplastic or thermosetting, or biostable, biodegradable, bioabsorbable or dissolvable.

Exemplary polymers include the following: polycarboxylic acid polymers and copolymers including polyacrylic acids (e.g., acrylic latex dispersions and various polyacrylic acid products such as HYDROPLUS, available from Boston Scientific Corporation, Natick Mass. and described in U.S. Pat. No. 5,091,205, the disclosure of which is hereby incorporated herein by reference, and HYDROPASS, also available from Boston Scientific Corporation); acetal polymers and copolymers; acrylate and methacrylate polymers and copolymers; cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polybismaleinimides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); anhydride polymers and copolymers including maleic anhydride polymers; polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-butadiene copolymers, acrylonitrile-styrene copolymers, acrylonitrile-butadiene-styrene copolymers, styrene-butadiene-styrene copolymers and styrene-isobutylene-styrene copolymers, polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates (e.g., U.S. Pat. No. 5,091,205 describes medical devices coated with one or more polyisocyanates such that the devices become instantly lubricious when exposed to body fluids); polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes (e.g., BAYHYDROL polyurethane dispersions); p-xylylene polymers; polyiminocarbonates; copoly(etheresters)such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and copolymers of the above.

Preferred polymers for use in connection with the present invention include ethylene-vinyl acetate copolymers (EVA) and polyurethanes.

The polymer matrix portion can be formed using various known processes. For example, the polymer matrix portion can be formed using solvent-based techniques in which the polymer is first dissolved in a solvent, after which the polymer solution is used to form the matrix portion. The solvent should, of course, be compatible with the polymer. Preferred techniques of this nature include solvent casting, spin coating, web coating, solvent spraying, dipping, fiber forming, ink jet techniques and combinations of these processes. If desired, coating techniques can be repeated or combined to build up the polymer matrix portion to the desired thickness. In many cases, the solution is applied to a template, and the polymer matrix portion is obtained, after solvent elimination, by simply removing the polymer from the template. Such techniques are particularly appropriate for forming simple objects such as sheets, tubes, cylinders and so forth.

When forming the matrix portion using solvent-based techniques, so long as it is compatible, the antimicrobial agent can be provided within the polymer/solvent mixture, for example, in dissolved form or as a particulate suspension. Such techniques allow the antimicrobial agent to be loaded concurrently with polymer matrix formation.

As another example, the polymer matrix can be provided in final shape by casting processes in which a mold or other receptacle is provided with liquid monomer, whereupon the monomer becomes cured (for example by the application of heat, ultraviolet light, atmospheric exposure, etc.) Similar to solvent-based techniques, so long as the antimicrobial agent is compatible with the liquid monomer, the antimicrobial agent can be provided within the liquid monomer at the time of polymer matrix formation, allowing the antimicrobial agent to be loaded concurrently with polymer matrix formation.

As yet another example, in the case where a thermoplastic polymer is selected as the polymer matrix material, a variety of standard thermoplastic processing techniques for device formation can be used, including compression molding, injection molding, blow molding, spinning, vacuum forming and calendaring, thermoforming and rot ational molding, as well as extrusion into sheets, fibers, rods, tubes and other cross-sectional profiles of various lengths. Assuming that the antimicrobial agent to be loaded within the matrix is stable at processing temperatures, then it can be combined with the polymer prior to thermoplastic processing, for example, by extrusion.

The antimicrobial agent can also be provided within the polymer matrix after the polymer matrix portion is formed, for example, using one of the techniques described above. For instance, the antimicrobial agent can be first dissolved in a solvent that is compatible with both the polymer matrix and the antimicrobial agent. Subsequently, the thus-formed solution is contacted with the polymer matrix portion, whereupon the antimicrobial agent is loaded into the polymer matrix portion, for example, by diffusion into the matrix. For this purpose, the polymer matrix portion can be immersed or dipped into the solution; the solution can be applied to the polymer matrix, for example, by spraying; and so forth. The polymer matrix portion can subsequently be dried, with the antimicrobial agent remaining therein.

Figure 3:
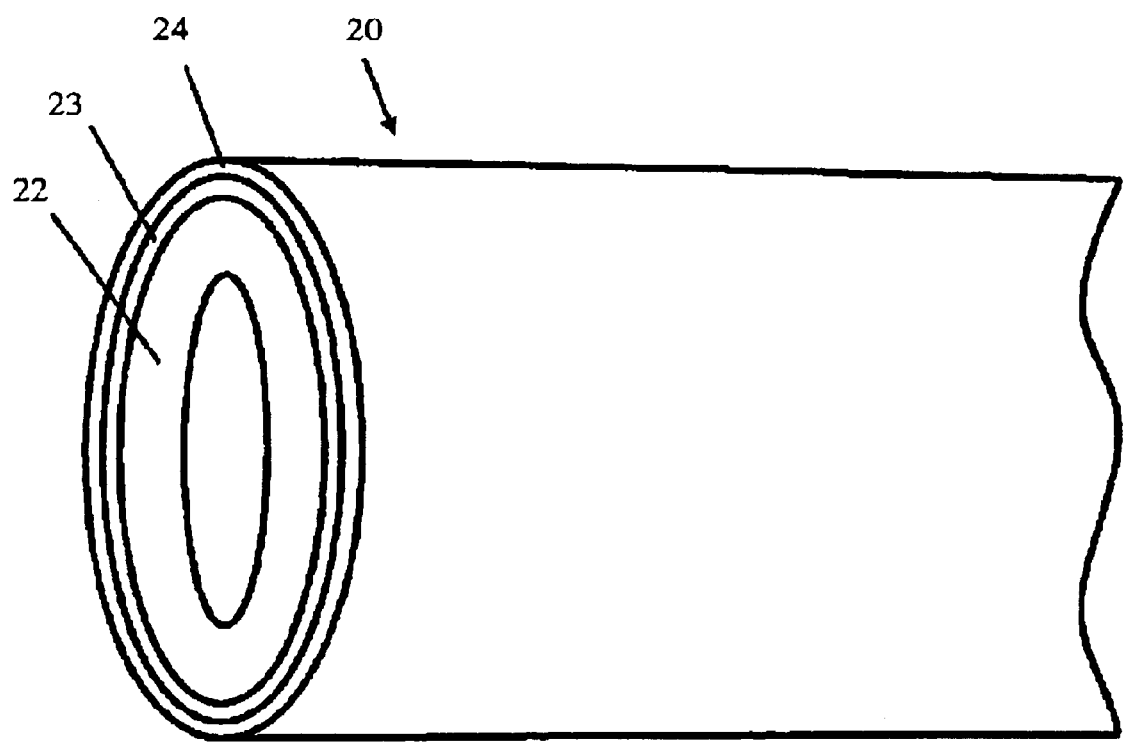

It also may be useful to coat the polymer matrix portion with an additional polymer layer, which may serve, for example, as a barrier layer to retard diffusion of the antimicrobial agent and extend release time. For example, the barrier layer may be selected from those polymer materials discussed above that are effective to retard diffusion. An example of a medical device design that embodies this approach is presented in FIG. 3. As in FIG. 2 above, the medical device, represented by the numeral 20, includes a polymer matrix 22 and a surfactant region 24. However, FIG. 3 further contains a barrier layer 23, between the polymer matrix 22 and surfactant region 24. Other techniques for extending the release time of the antimicrobial agent include maximizing polymer matrix depth and choosing antimicrobial agents with low solubility.

Preferred compounds for use in connection with the surfactant regions of the devices of the present invention include biosurfactants and surfactant polymers, among others.

"Surfactant polymers" as defined herein are polymers having both hydrophobic and hydrophilic groups that bring about a reduction in the surface tension of liquids, most notably aqueous-based liquids. Preferred surfactant polymers for use in connection with the present invention include oligosaccharide surfactant polymers and surfactant polymers having a poly(vinyl amine) backbone with hydrophilic poly(ethylene oxide), and hydrophobic hexanal side chains, such as those described in Vacheethasanee et al, "Surfactant polymers designed to suppress bacterial (*Staphylococcus epidermidis*) adhesion on biomaterials", J. Biomed. Mater. Res., 50, pp. 302–312, 2000, the entire disclosure of which is hereby incorporated by reference in its entirety. Examples include poly(N-vinyl monomethoxy poly(ethylene oxide) ethylamine-co-N-vinyl hexylamine), which may be uncapped or capped, for example, with acetaldehyde, and poly(N-vinyl dextran aldonamide-co-N-vinyl alkanamide).

"Biosurfactants" as defined herein are agents produced by microorganisms and other biological sources (e.g., plants) that bring about a reduction in the surface tension of liquids, most notably aqueous-based liquids.

Biosurfactants are commonly distinguished according to their chemical structure. Preferred classes of biosurfactants include glycolipids, lipopeptides, depsipeptides, phospholipids, substituted fatty acids, lipopolysaccharides, and cyclic lipopeptides.

Preferred biosurfactants for the practice of the present invention include surlactin, a biosurfactant produced by *Lactobacillus acidophilus*, surfactin, a lipopeptide biosurfactant produced by *Bacillus subtilis*, rhamnolipids, rhamnose-containing glycolipid biosurfactants produced by, for example, *Pseudomonas aeruginosa* and available from Jeneil Biosurfactant Company, visconsin, a cyclic depsipeptide, Iturin A, produced by *Bacillus subtilis*, as well as analogs of the same Combinations of biosurfactants as well as combinations that include a biosurfactant and a synthetic surfactant are also contemplated.

The surfactant region can be provided over the polymer matrix portion using various known processes. For example, a coating consisting of the surfactant can be directly applied over the polymer matrix portion, a coating containing the surfactant along with various desired adjuvant materials can be applied over the polymer matrix portion, and so forth. Attachment of the surfactant to the underlying support (e.g., the polymer matrix or a barrier layer disposed over the polymer matrix) can be strengthened by means of covalent coupling techniques. Such techniques are well known. The ultimate coupling system that is selected will be dependent, for example, upon the chemical nature of the specific polymer matrix and upon the antimicrobial agent selected. The surfactant can also be linked to the underlying support by a number of other means, including hydrophobic interactions and ionic interactions.

Once the surfactant is applied over the antimicrobial-agent-containing polymer matrix, the medical device is ready for long-term implantation.

In conclusion, the present invention provides compositions that are appropriate for use in connection with long-term indwelling medical devices. Although the present invention has been described with respect to several exemplary embodiments, there are many other variations of the above-described embodiments that will be apparent to those skilled in the art, even where elements have not explicitly been designated as exemplary. It is understood that these modifications are within the teaching of the present invention, which is to be limited only by the claims appended hereto.

What is claimed is:

1. A medical device comprising:
    a reservoir comprising (a) a polymer matrix and (b) an antimicrobial agent disposed within said polymer matrix, said reservoir adapted for long-term release of said antimicrobial agent from said polymer matrix; and
    a surfactant region comprising a surfactant, said surfactant region disposed over said reservoir at an outer surface of said medical device;
    wherein said reservoir is not a coating layer on said medical device; and
    wherein said medical device is a urine contacting device adapted for long-term implantation within the body of a patient.

2. The medical device of claim 1, wherein said surfactant region comprises a biosurfactant.

3. The medical device of claim 2, wherein said biosurfactant is selected from glycolipids, lipopeptides, depsipeptides, phospholipids, substituted fatty acids, and lipopolysaccharides.

4. The medical device of claim 2, wherein said biosurfactant is selected from surlactin, surfactin, visconsin and rhamnolipids.

5. The medical device of claim 1, wherein said surfactant is a surfactant polymer.

6. The medical device of claim 5, wherein said surfactant polymer is a surfactant polymer having a poly(vinyl amine) backbone and having hydrophilic poly(ethylene oxide) and hydrophobic hexanal side chains.

7. The medical device of claim 1, wherein said surfactant is linked to said outer surface by one or more interactions selected from hydrophobic interactions, ionic interactions and covalent interactions.

8. The medical device of claim 1, wherein said medical device is selected from a ureteral stent and a urethra catheter.

9. The medical device of claim 1, wherein said antimicrobial agent is selected from triclosan, chlorhexidine, silver sulfadiazine, silver ions, benzalkonium chloride and zinc pyrithione.

10. The medical device of claim 1, wherein said antimicrobial agent is a broad-spectrum antibiotic.

11. The medical device of claim 1, wherein said antimicrobial agent is an antiseptic agent.

12. The medical device of claim 11, wherein said antiseptic agent is iodine.

13. The medical device of claim 1, wherein said polymer matrix comprises a polymer selected from an ethylene-vinyl acetate copolymer and a polyurethane.

14. A method of treatment comprising:
    providing the urine contacting medical device of claim 1; and
    implanting said urine contacting medical device within the body of a patient for a period of at least three months.

15. The method of claim 14, wherein said surfactant is a biosurfactant.

16. The method of claim 14, wherein said surfactant is a surfactant polymer.

17. The method of claim 14, wherein said polymer matrix comprises a polymer selected from an ethylene-vinyl acetate copolymer and a polyurethane.

18. A method of constructing the medical device of claim 1, comprising:
    forming said reservoir; and
    providing a surfactant region comprising a surfactant over said reservoir at an outer surface of said medical device.

19. The method of claim 18, wherein said antimicrobial agent is disposed within said polymer matrix at the time of formation of said polymer matrix.

20. The method of claim 19, wherein said antimicrobial agent is co-cast with said polymer matrix.

21. The method of claim 19, wherein said antimicrobial agent is co-extruded with said polymer matrix.

22. The method of claim 18, wherein said antimicrobial agent is provided within said polymer matrix by imbibing said antimicrobial agent into said polymer matrix.

23. The method of claim 18, wherein said surfactant is a biosurfactant.

24. The method of claim 18, wherein said surfactant is a surfactant polymer.

25. The method of claim 18, wherein said surfactant is covalently linked at said outer surface of said device.

26. The method of claim 18, wherein said antimicrobial agent is selected from triclosan, chlorhexidine, silver sulfadiazine, silver ions, benzalkonium chloride and zinc pyrithione.

27. The medical device of claim 1, wherein said reservoir is in the form of a tubular medical device component, and wherein said surfactant region is provided in the form of a layer disposed over said reservoir.

28. The medical device of claim 27, wherein said tubular medical device component is selected from a stent body and a catheter tube.

* * * * *

UNITED STATES PATENT AND TRADEMARK OFFICE
CERTIFICATE OF CORRECTION

PATENT NO.    : 6,921,390 B2
DATED         : July 26, 2005
INVENTOR(S)   : Weenna Bucay-Couto et al.

It is certified that error appears in the above-identified patent and that said Letters Patent is hereby corrected as shown below:

Column 1,
Line 60, after "preferred", change "biosurfactant" to -- biosurfactants --.

Column 5,
Line 54, before "molding", change "rot ational" to -- rotational --.

Column 6,
Line 63, after "same", change "Combinations", to -- combinations --.

Column 8,
Line 2, before "catheter", change "urethra" to -- urethral --.

Signed and Sealed this

Twentieth Day of December, 2005

JON W. DUDAS
*Director of the United States Patent and Trademark Office*